United States Patent
Broggini et al.

(10) Patent No.: US 10,100,035 B2
(45) Date of Patent: Oct. 16, 2018

(54) SUBSTITUTED 2-[3-(1-METHYL-PIPERIDIN-4-YL)-PROPYLAMINO]-PYRIMIDINE-5-CARBOXYLIC ACIDS AND AMIDES AND METHODS OF MAKING THE SAME

(71) Applicant: Janssen Pharmaceutica NV, Beerse (BE)

(72) Inventors: Diego Broggini, Zürich (CH); Matteo Conza, Thayngen (CH); Oliver Flögel, Zürich (CH); Stefan Horns, Schaffhausen (CH); Susanne Lochner, Singen (DE); Guangrong Tang, Chongqing (CN); Zhaobin Wang, Chongqing (CN); Lucie Lovelle, Basel (CH)

(73) Assignee: Janssen Pharmaceutica NV, Beerse (BE)

(*) Notice: Subject to any disclaimer, the term of this patent is extended or adjusted under 35 U.S.C. 154(b) by 0 days.

(21) Appl. No.: 15/710,688

(22) Filed: Sep. 20, 2017

(65) Prior Publication Data

US 2018/0009783 A1 Jan. 11, 2018

Related U.S. Application Data

(62) Division of application No. 15/341,022, filed on Nov. 2, 2016, now Pat. No. 9,796,699.

(60) Provisional application No. 62/250,005, filed on Nov. 3, 2015.

(51) Int. Cl.
| | | |
|---|---|---|
| *C07D 401/12* | (2006.01) | |
| *C07D 211/26* | (2006.01) | |
| *C07D 213/57* | (2006.01) | |
| *C07D 401/14* | (2006.01) | |

(52) U.S. Cl.
CPC .......... *C07D 401/12* (2013.01); *C07D 211/26* (2013.01); *C07D 213/57* (2013.01); *C07D 401/14* (2013.01)

(58) Field of Classification Search
CPC ............ C07D 4014/12; C07D 4014/14; C07D 211/26; C07D 213/57
See application file for complete search history.

(56) References Cited

U.S. PATENT DOCUMENTS

| | | | |
|---|---|---|---|
| 7,507,737 B2 * | 3/2009 | Edwards | C07D 401/14 514/255.05 |
| 8,598,189 B2 | 12/2013 | Edwards et al. | |
| 8,835,633 B2 * | 9/2014 | Cesco-Cancian | C07D 403/04 544/331 |
| 8,921,550 B2 | 12/2014 | Mani et al. | |
| 9,371,311 B2 * | 6/2016 | Mani | C07D 403/04 |
| 2008/0306082 A1 | 12/2008 | Dahnke et al. | |
| 2010/0029942 A1 | 2/2010 | Cesco-Cancian et al. | |
| 2017/0121309 A1 | 5/2017 | Broggini et al. | |

FOREIGN PATENT DOCUMENTS

WO WO 2009/156484 A2 12/2009

OTHER PUBLICATIONS

Berge et al., "Pharmaceutical Salts", *Journal of Pharmaceutical Sciences*, vol. 66, No. 1 (Jan. 1977), pp. 1-19.
Greene et al., *Protective Groups in Organic Synthesis*, Third Edition, 1999, Table of Contents and Index.
Kocienski, *Protecting Groups*, Thieme Verag, New York, N.Y., 1994, Table of Contents.
Stahl et al., "Handbook of Pharmaceutical Salts, Properties, Selection and Use", International Union of Pure and Applied Chemistry, Zurich 2002, Table of Contents.
Communication Relating to the Results of the Partial International Search dated Dec. 13, 2016, for Corresponding International Application PCT/EP2016/076405.
International Search Report and Written Opinion dated Feb. 13, 2017, for Corresponding International Application PCT/EP2016/076405.

* cited by examiner

*Primary Examiner* — Alexander R Pagano
*Assistant Examiner* — Ebenezer O Sackey

(57) ABSTRACT

The present invention relates to certain intermediates useful in the preparation of certain benzoimidazol-2-yl pyrimidines and processes for preparing them. In particular, the present invention relates to various 2-[3-(1-methyl-piperidin-4-yl)-propylamino]-pyrimidine-5-carboxylic acids and amides as useful intermediates in the preparation of compounds including

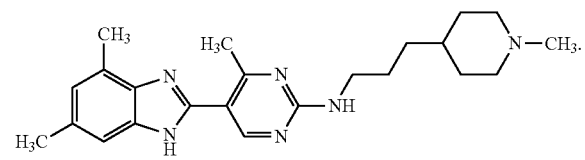

[5-(4,6-Dimethyl-1H-benzoimidazol-2-yl)-4-methyl-pyrimidin-2-yl]-[3-(1-methyl-piperidin-4-yl)-propyl]-amine

4 Claims, No Drawings

SUBSTITUTED 2-[3-(1-METHYL-PIPERIDIN-4-YL)-PROPYLAMINO]-PYRIMIDINE-5-CARBOXYLIC ACIDS AND AMIDES AND METHODS OF MAKING THE SAME

CROSS REFERENCE TO RELATED APPLICATIONS

This application is a divisional application of U.S. Ser. No. 15/341,022 filed Nov. 2, 2016, which claims the benefit of U.S. Provisional Application 62/250,005 filed Nov. 3, 2015.

GOVERNMENT RIGHTS

Not applicable

TECHNICAL FIELD

The present invention relates to intermediates useful in the preparation of benzoimidazol-2-yl pyrimidines and processes for preparing them. In particular, the present invention relates to various 2-[3-(1-methyl-piperidin-4-yl)-propylamino]-pyrimidine-5-carboxylic acids and amides as useful intermediates in the preparation of compounds including

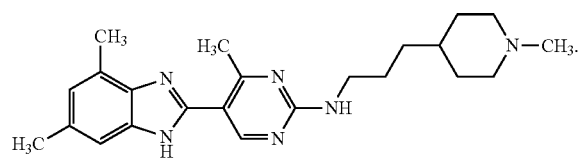

[5-(4,6-Dimethyl-1H-benzoimidazol-2-yl)-4-methyl-pyrimidin-2-yl]-[3-(1-methyl-piperidin-4-yl)-propyl]-amine

BACKGROUND

Benzoimidazol-2-yl pyrimidines are useful compounds for modulating $H_4$ receptor activity, and so for the treatment of disease states, disorders, and conditions mediated by $H_4$ receptor activity, including allergy, asthma, autoimmune diseases, and pruritis. Such compounds, and their methods of use, are described inter alia in U.S. Pat. No. 8,598,189, which is incorporated by reference herein in its entirety.

SUMMARY

Certain embodiments of the present invention provide for compounds having structures according to Formula (VI)

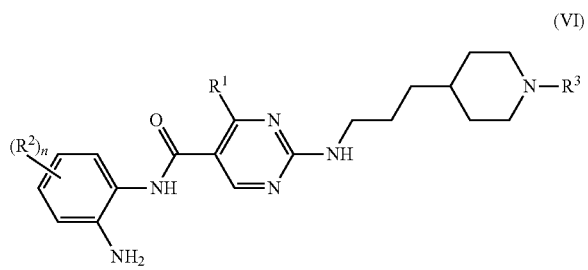

wherein
R$^1$ is H or alkyl;
each R$^2$ is independently H, chloro, fluoro, or alkyl;
each R$^3$ is independently an alkyl or amine protecting group; and
n is 1, 2, 3, or 4,
including compounds of Formula (VI-A2) and Formula (VI-B2):

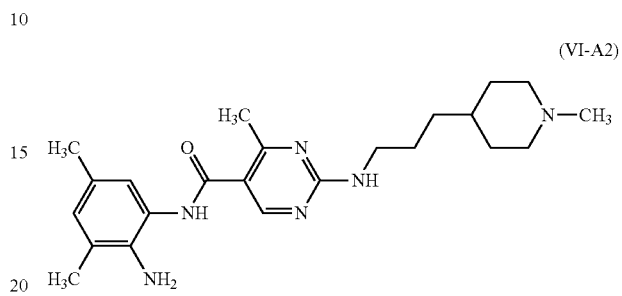

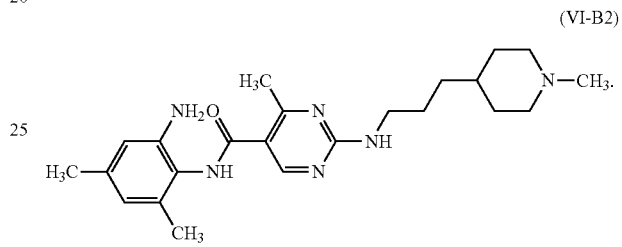

Other embodiments provide for compounds having a structure of Formula (IV)

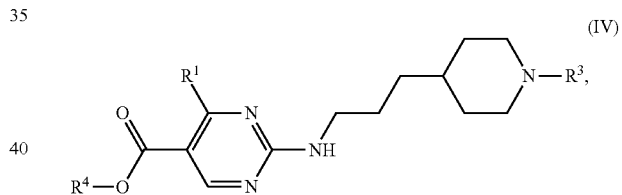

wherein
R$^1$ is H or alkyl;
R$^3$ is alkyl or an amine protecting group; and
R$^4$ is H, alkyl, or other acid protecting group,
including compounds of Formulae (IV-1) and (IV-2):

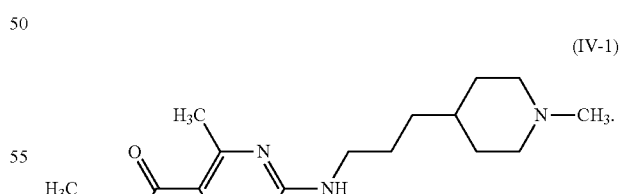

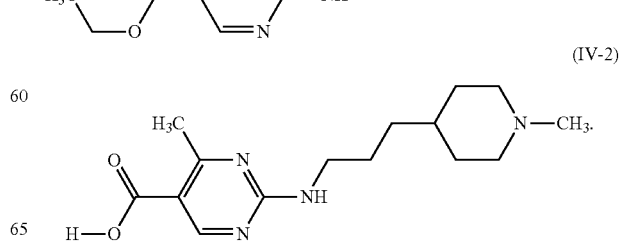

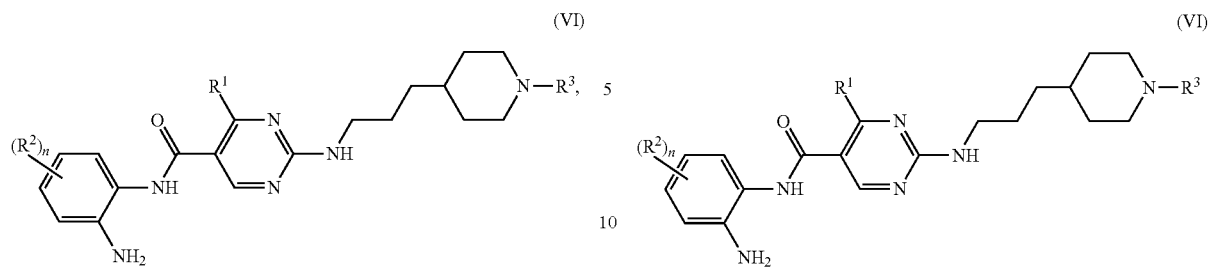

comprising reacting a compound of Formula (V), or a salt thereof, with a compound of Formula (IV) for a time and under conditions effective to form the compound of Formula (VI)

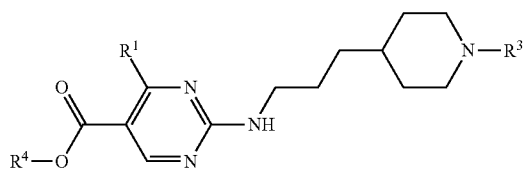

wherein
  $R^1$ is H or alkyl;
  each $R^2$ is independently H, chloro, fluoro, or alkyl;
  each $R^3$ is independently alkyl or an amine protecting group;
  $R^4$ is H, alkyl, or another acid protecting group; and
  n is 1, 2, 3, or 4.

In particular embodiments, the compound of Formula (V) is a compound of Formula (V-1):

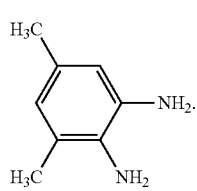

Still other embodiments provide methods of converting a compound of Formula (VI) to a compound of Formula (VII):

including converting a compound of Formula (VI-A1) to a compound of Formula (VII-1) and a compound of Formula (VI-B1) to a compound of Formula (VII-1):

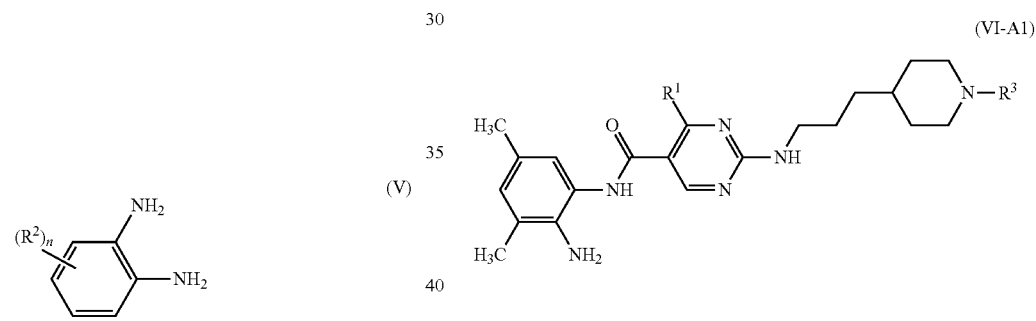

and specifically converting a compound of Formula (VI-A2) to a compound of Formula (VII-2) and a compound of Formula (VI-B2) to a compound of Formula (VII-2):

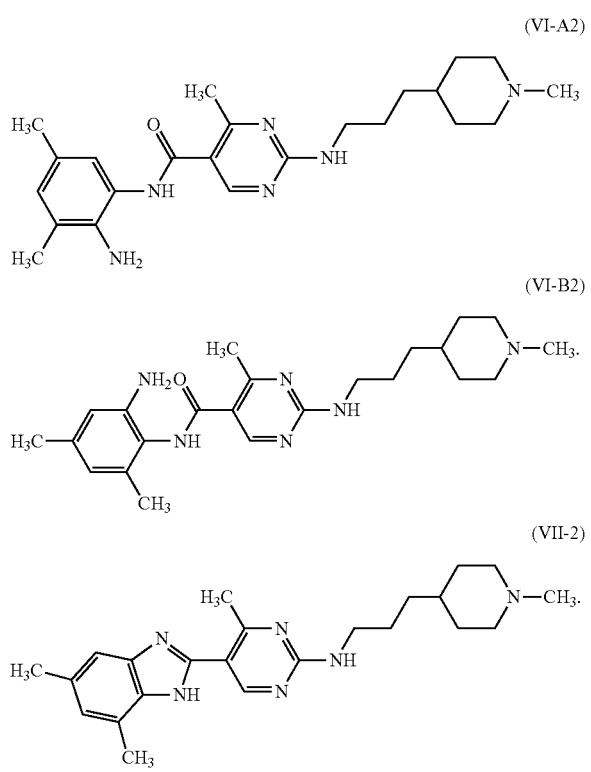

BRIEF DESCRIPTION OF THE DRAWINGS

Not applicable

DETAILED DESCRIPTION OF ILLUSTRATIVE EMBODIMENTS

The present invention may be understood more readily by reference to the following description taken in connection with the accompanying—Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to the compounds and associated derivatives and to the methods of preparing the compounds, as well as the use of the compounds so prepared.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step or part may also be considered an independent embodiment in itself.

Terms

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH(s), R—COOH(sol), and R—COO⁻(sol). In this example, R—COOH(s) refers to the solid compound, as it could be for example in a tablet or some other solid pharmaceutical composition or preparation; R—COOH(sol) refers to the undissociated form of the compound in a solvent; and R—COO⁻(sol) refers to the dissociated form of the compound in a solvent, such as the dissociated form of the compound in an aqueous environment, whether such dissociated form derives from R—COOH, from a salt thereof, or from any other entity that yields R—COO⁻ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In this regard, if such entity is for example in an aqueous environment, it is understood that the compound R—COOH is in such same medium, and therefore the entity is being exposed to species such as R—COOH(aq) and/or R—COO⁻(aq), where the descriptor "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. In another example, a zwitterionic compound is encompassed herein by referring to a compound that is known to form zwitterions, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. (See, for example its on-line version at http://www.ebi.ac.uk/chebi/init.do). As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are always or necessarily given explicitly herein. They are, however, part of the embodiments of this invention. No further examples in this regard are necessary because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively.

Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

An "alkyl" group refers to an aliphatic hydrocarbon group. The alkyl group may be branched or straight chain. The "alkyl" group may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). In one aspect the alkyl is selected from the group consisting of methyl, ethyl, propyl, iso-propyl, n-butyl, isobutyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, and the like. In some embodiments, an alkyl is a $C_{1-6}$ alkyl. In some preferred embodiments, an alkyl is methyl or ethyl.

Various embodiments of the present invention provide various compounds directed to the general synthesis of:

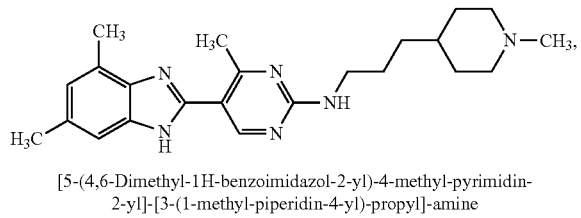 [SMILES: Cc1cc(C)c2nc(-c3cnc(NCCCC4CCN(C)CC4)nc3C)[nH]c2c1]

[5-(4,6-Dimethyl-1H-benzoimidazol-2-yl)-4-methyl-pyrimidin-2-yl]-[3-(1-methyl-piperidin-4-yl)-propyl]-amine and compounds, solvates, and salts related thereto. Throughout this specification, while descriptions are made in terms of specific compounds and intermediates, it should be appreciated that these descriptions include the salts, solvates (including hydrates), or salts and solvates of these compounds. Additional embodiments provide that these salts, solvates (including hydrates), or salts and solvates include those which are pharmaceutically acceptable, for use in mammals, especially for use in humans.

The descriptions of specific compounds also include, as separate embodiments, those compounds in which amine and/or carboxylic acids are protected by protecting groups. Protecting groups or protective groups are those introduced into a molecule by chemical modification of a functional group to obtain chemoselectivity in a subsequent chemical reaction. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts", *J. Pharm. Sci.*, 1977, 66:1-19, and Handbook of Pharmaceutical Salts, Properties, Selection, and Use, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propanoates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound described herein contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound described herein is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

Some embodiments of the present invention include compounds having a structure of Formula (VI)

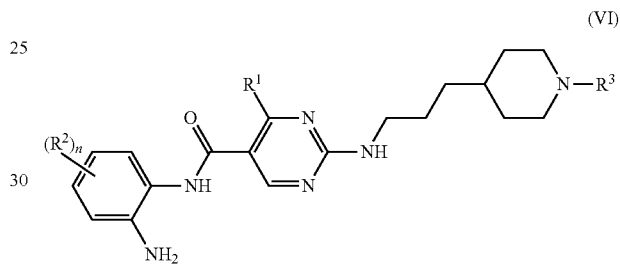

(VI)

wherein
R$^1$ is H or alkyl (preferably C$_{1-6}$ alkyl);
each R$^2$ is independently H, chloro, fluoro, or alkyl (preferably C$_{1-6}$ alkyl);
each R$^3$ is independently alkyl (preferably C$_{1-6}$ alkyl) or an amine protecting group; and
n is 1, 2, 3, or 4, preferably 2.

The term "amine protecting group" is described elsewhere in this application, and includes such exemplary protecting groups as carbobenzyloxy (Cbz) group, p-methoxybenzyl carbonyl (Moz or MeOZ) group, tert-butyloxycarbonyl (BOC) group, 9-fluorenylmethyloxycarbonyl (FMOC), acetyl (Ac) group, benzoyl (Bz) group, benzyl (Bn) group, carbamate group, p-methoxybenzyl (PMB), 3,4-dimethoxybenzyl (DMPM), p-methoxyphenyl (PMP) group, and tosyl (Ts) group.

Within this structure, additional independent embodiments further provide that R$^1$ is methyl.

Within this structure, additional independent embodiments further provide that R$^3$ is methyl.

Within this structure, additional independent embodiments further provide that R$^2$ is independently methyl or H.

Still further embodiments provide compounds, or mixtures of compounds, having a structure of Formula (VI-A1) or of Formula (VI-B1), or a salt, hydrate, or salt and hydrate thereof, with such formulae as defined above.

Other specific embodiments include the compounds, or mixtures of compounds, having a structure of Formula (VI-A2) or of Formula (VI-B2), or a salt, hydrate, or salt and hydrate thereof, with such formulae as defined above.

Other embodiments provide compounds having a structure of Formula (IV)

(IV)

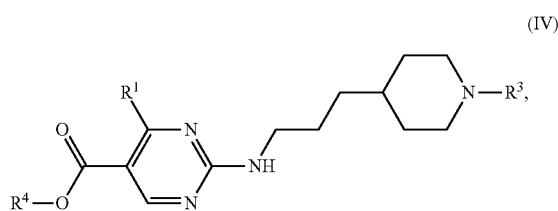

wherein

R¹ is H or alkyl (preferably $C_{1-6}$ alkyl);

R³ is alkyl (preferably $C_{1-6}$ alkyl) or an amine protecting group; and

R⁴ is H, alkyl (preferably $C_{1-6}$ alkyl), or another acid protecting group.

The term "amine protecting group" is used as described and exemplified elsewhere in the specification. The term "acid protecting group" is also described elsewhere in this application, and includes such protecting groups as a methyl ester, benzyl ester, tert-butyl esters, esters of 2,6-disubstituted phenols (e.g. 2,6-dimethylphenol, 2,6-diisopropylphenol, 2,6-di-tert-butylphenol), silyl esters, orthoesters, and oxazoline.

Within this structure, additional independent embodiments further provide that R¹ and R³ are methyl, and R⁴ is H, methyl, or ethyl.

Within this structure, additional independent embodiments further provide that R¹ is methyl. Other independent embodiments provide that R³ is methyl.

In one specific embodiment, the compound is one having a structure of Formula (IV-1), which structure is given above.

Still further embodiments provide a compound having a structure of Formula (IV-2), which structure is given above.

The compounds of Formula (VI)

(VI)

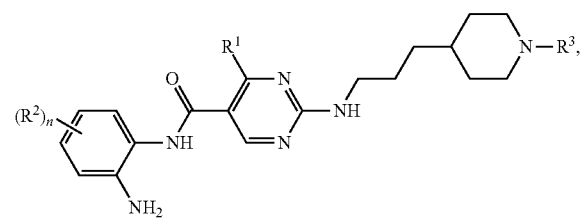

may be prepared by processes comprising: reacting a compound of Formula (IV), e.g., of Formula (IV-2), or a salt thereof, with a compound of Formula (V) for a time and under conditions effective to form the compound of Formula (VI)

(IV)

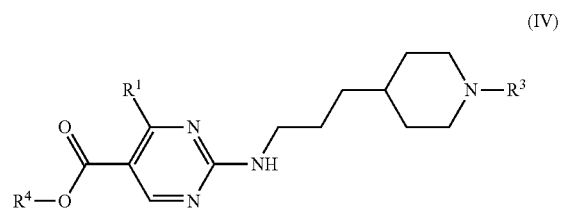

(V)

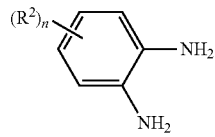

wherein

R¹ is H or alkyl (preferably $C_{1-6}$ alkyl);

each R² is independently H, chloro, fluoro, or alkyl (preferably $C_{1-6}$ alkyl);

each R³ is independently alkyl (preferably $C_{1-6}$ alkyl) or an amine protecting group;

R⁴ is H, alkyl (preferably $C_{1-6}$ alkyl), or another acid protecting group; and n is 1, 2, 3, or 4.

In such embodiments, respective compounds may be substituted such that R¹ and R³ are methyl, and R⁴ is H, methyl, or ethyl.

Such processes may also include those wherein the compound of Formula (V) is a compound of Formula (V-1):

(V-1)

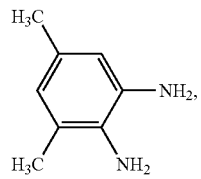

and the compound of Formula (VI) is of Formula (VI-A1) or Formula (VI-B1), whose structures are given above, or a mixture thereof.

In some embodiments, the methods comprise reacting any compound within the genus of Formula (IV), including a compound of Formula (IV-2) with a compound of Formula (V-1)

(IV-2)

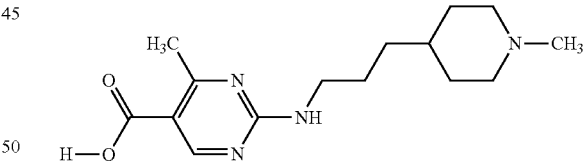

(V-1)

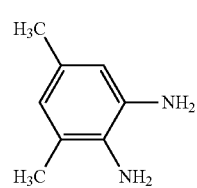

for a time and under conditions effective to form the corresponding product or products.

In these methods, it is convenient to use a coupling agent to facilitate the synthesis. Such coupling agents may include, but are not necessarily limited to, benzotriazol-1-yl-oxytripyrrolidinophosphonium hexafluorophosphate (PyBOP), O-(Benzotriazol-1-yl)-N,N,N',N'-tetramethyluronium tetrafluoroborate (TBTU), N,N'-

Dicyclohexylcarbodiimide (DCC), 1-ethyl-3-(-3-dimethylaminopropyl) carbodiimide or its hydrochloride (EDC HCl), hydroxybenzotriazole (HOBt), 1,1'-carbonyldiimidazole (CDI), thionyl chloride (SOCl$_2$) or a combination thereof. Such coupling agents are well known in the art for the purposes intended here, and the person of ordinary skill in the art would be well able to use them for this purpose without undue experimentation. Some specific experimental conditions useful in applying some of these coupling agents may be found in the Examples provided in this application.

Other embodiments provide that the compounds of Formula (IV),

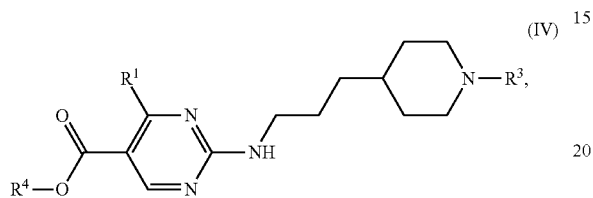

where $R^4$ is $C_{1-6}$ alkyl, can be prepared by methods comprising reacting a compound of Formula (II) with a compound of Formula (III) for a time and under conditions effective to form a compound of Formula (IV)

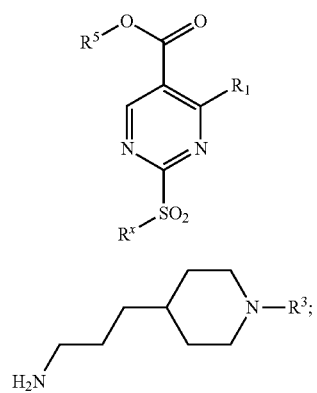

wherein $R^5$ and $R^x$ are independently $C_{1-6}$ alkyl. Non-limiting, exemplary conditions useful for such transformation may be found in the Examples.

The compound of Formula (II) can be prepared by selective oxidation of a compound of Formula (I).

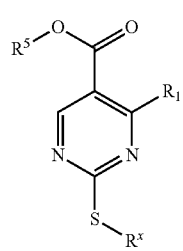

In some embodiments, the compound of Formula (I), (II), and (III) may be independently of Formula (I-1), (II-1), and (III-1), respectively:

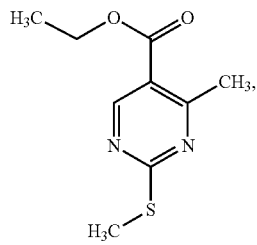

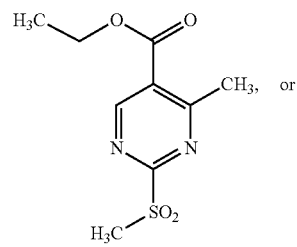

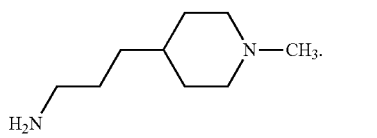

The transformation of any compound of the genus of Formula (I) to that of the corresponding compound of the genus of Formula (II) may be effected by treatment of the former with an oxidizing agent. The reaction of compound of Formula (II) with the compound of Formula (III) may be carried out by relying on in situ generation of the compound of Formula (II) or by relying on an isolated compound of Formula (II). Chemistries useful for transforming sulfides to sulphones are well-known in the art and the person of ordinary skill would be able to affect this transformation using any one of known oxidizing agents or oxidizing systems without undue experimentation. Each of the oxidizing agents capable of effecting these transformations is incorporated here. In one non-limiting example, the oxidizing agent comprises hydrogen peroxide, perfluoroacyl peracids, aryl peracids (e.g., m- or p-chlorobenzoic peracid), ammonium molybdates (including ammonium heptamolybdate (NH$_4$)$_6$Mo$_7$O$_{24}$) or other molybdates), or a combination thereof. Other such oxidizing agents comprise permanganate, and 1,3,5-triazo-2,4,6-triphosphorine-2,2,4,4,6,6-tetrachloride (TAPC).

Methods of the present invention also provide that the compounds of the genus of Formula (VI) may be further converted to the corresponding compounds of Formula (VII), for example, the compound of Formula (VI-A1) or Formula (VI-B1) may be further converted to a compound of Formula (VII-1):

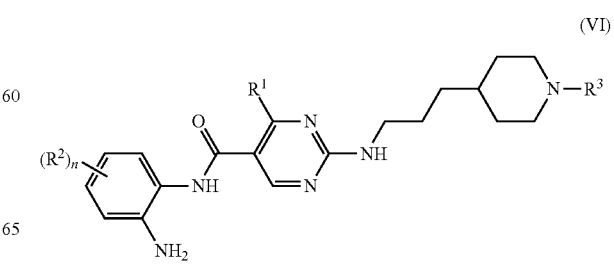

(VII)

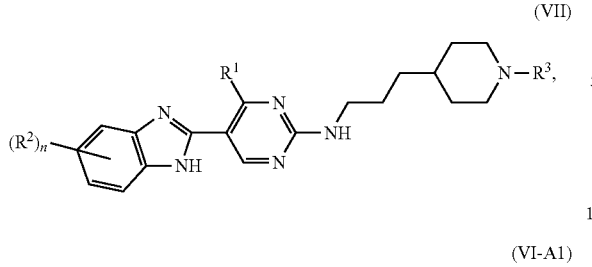

(VI-A1)

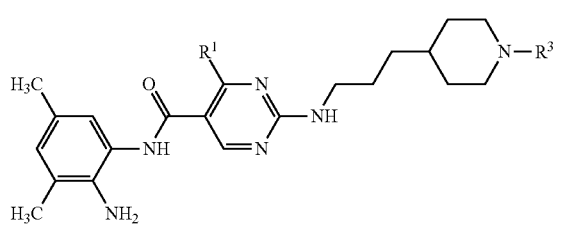

(VI-B1)

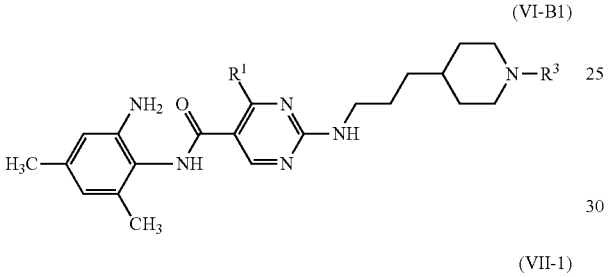

(VII-1)

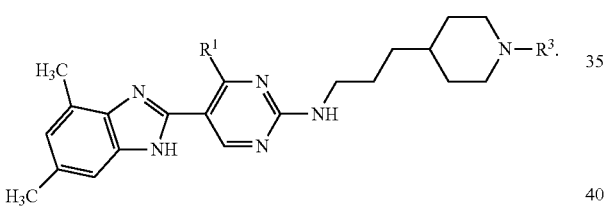

More specifically, a compound of Formula (VI-A2) or of Formula (VI-B2), or mixtures thereof, may be converted to the corresponding compound of Formula (VII-2):

(VI-A2)

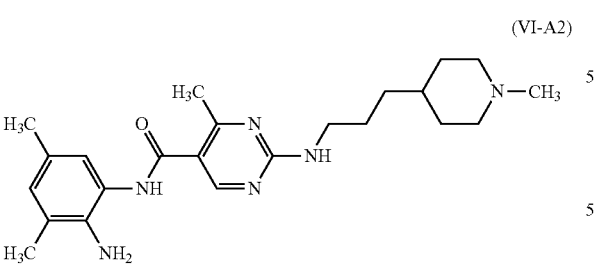

(VI-B2)

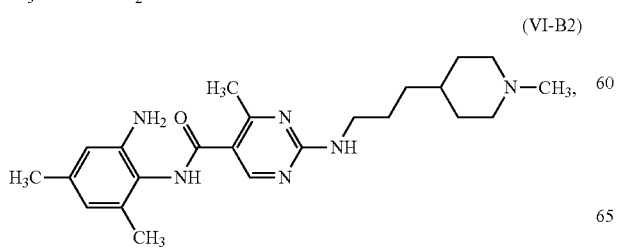

(VII-2)

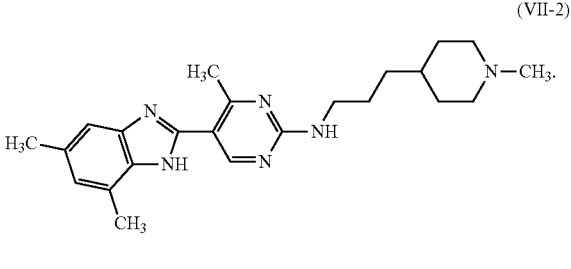

Such cyclizations may be done by the application of heat and/or with the use of an acid catalyst.

One of ordinary skill in the art will notice that compounds of formula (VII-1), such as compound of formula (VII-2), may be represented in more than one form. One of such forms is illustrated by the form shown in such formulae above. Another form is illustrated by the following respectively same formulae (VII-1') and (VII-2') due to the rotation about the bond that links the benzoimidazolyl and pyrimidinyl moieties, as illustrated in the drawing below:

(VII-1')

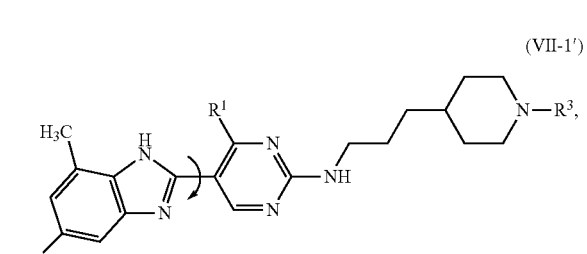

(VII-2')

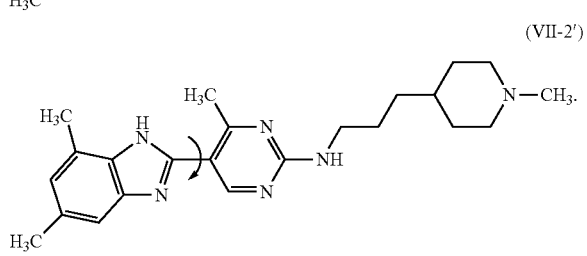

EXAMPLES

The following Examples are provided to illustrate some of the concepts described within this disclosure. While each Example is considered to provide a specific individual embodiment of composition, or methods of preparation and use, none of the Examples should be considered to limit the more general embodiments described herein.

In a broader context, the inventions described herein may be viewed, in part or in whole, as part of a general reaction scheme in preparing

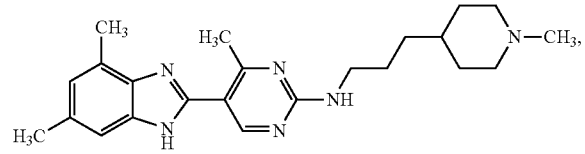

[5-(4,6-Dimethyl-1H-benzoimidazol-2-yl)-4-methyl-pyrimidin-2-yl]-
[3-(1-methyl-piperidin-4-yl)-propyl]-
amine according to a representative synthetic scheme:
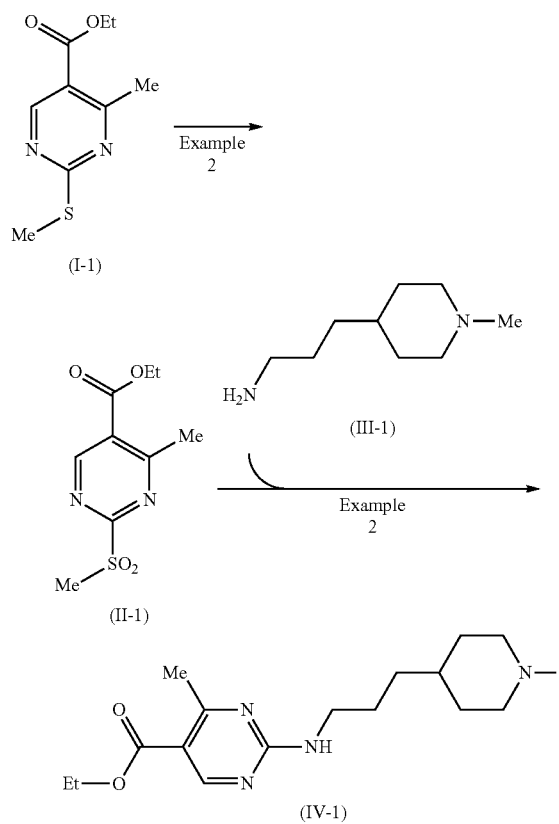
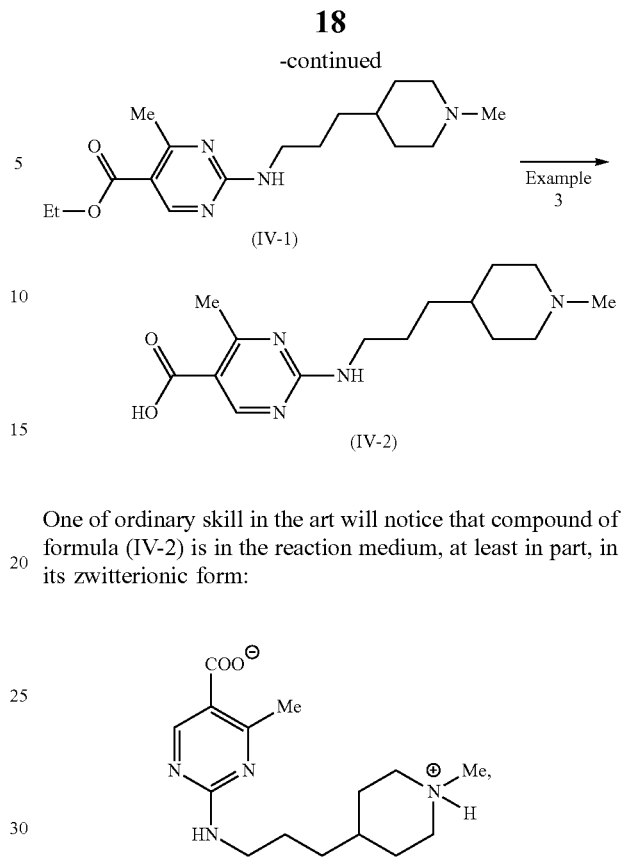
One of ordinary skill in the art will notice that compound of formula (IV-2) is in the reaction medium, at least in part, in its zwitterionic form:
and as noted above, the term "formula (IV-2)" or "compound (IV-2)" encompasses also this form.
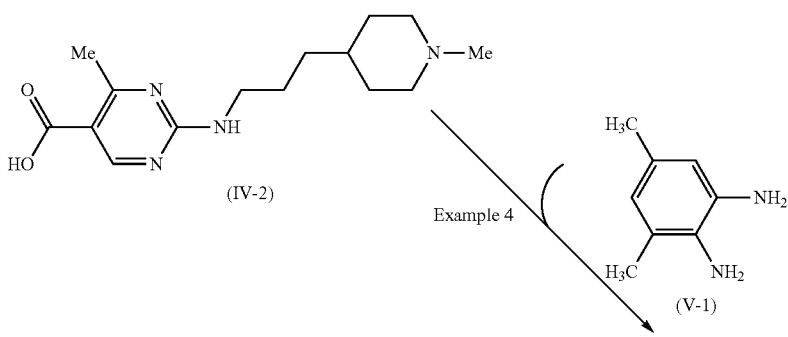
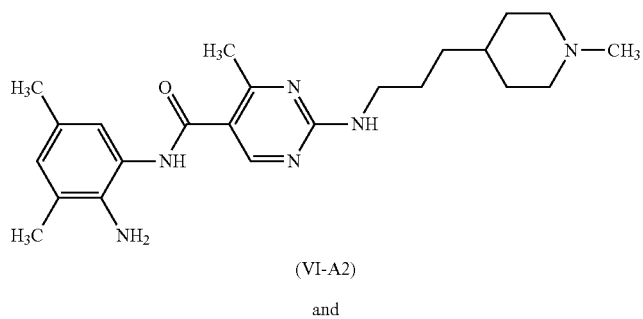
and

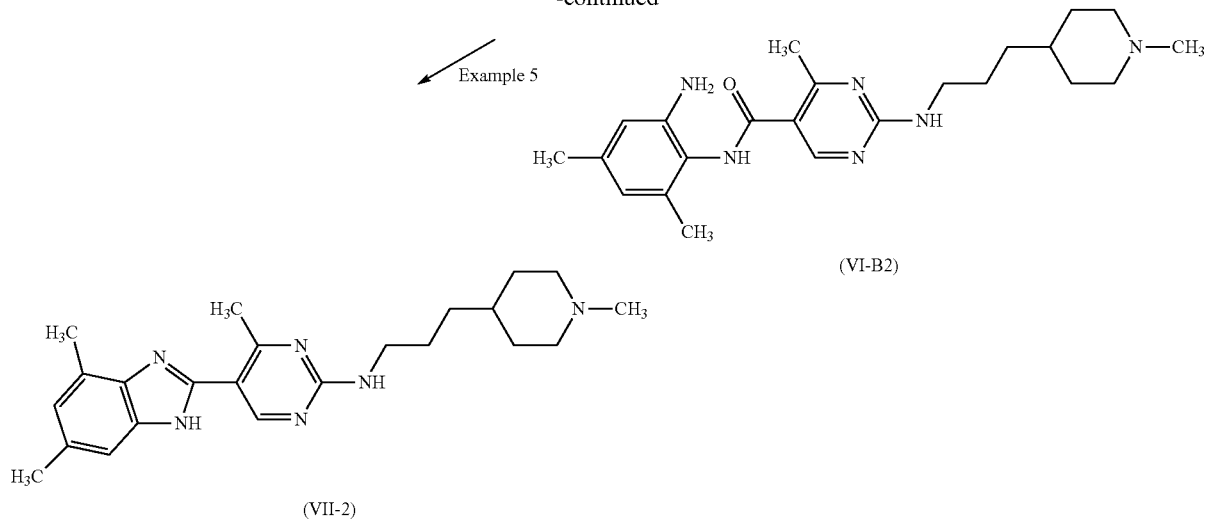

(VI-B2)

(VII-2)

Example 1. Syntheses of 3-(1-methylpiperidin-4-yl)propan-1-amine), Compound (III-1 or T133)

Compound III-1 is known. Some individual synthetic steps described in this example 1, such as coupling reactions and decarboxylation reactions, are known as general types of organic chemistry reactions. The combination of such steps to synthesize compound III-1 as presently discovered, however, has been found in the context of the present inventive work to provide a reliable synthesis of compound III-1 with significant minimization of side reactions with respect to other methods while using common and inexpensive reagents.

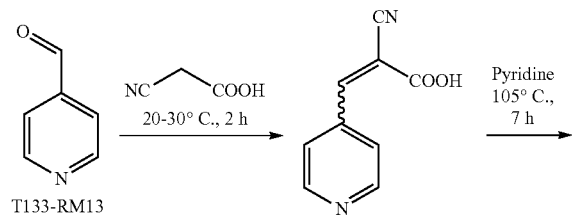

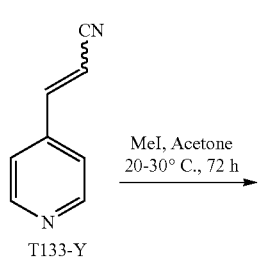

2-Cyanoacetic acid (113 g, 1.33 mol) was added to a solution of sodium carbonate (141 g, 1.33 mol) in water (1.5 L) at 20° C. The mixture was stirred at 15-20° C., then 4-pyridinecarbaldehyde (117 g, 1.09 mol) was added slowly. The mixture was stirred at 20° C. for 2-3 h, then conc. hydrochloric acid (200 mL) was added to adjust the pH to 2-3. The mixture was stirred at 25° C. for 1 h, then the resulting precipitate (T133-U, mixture of E- and Z-isomer) was isolated by filtration, washed with water and MTBE (methyl ter-butyl ether) and dried (dry product: 168 g).

The dry intermediate (168 g, 0.96 mol) was dissolved in pyridine (670 mL). The mixture was heated to 90° C. for 0.5 h, then to reflux (105-110° C.) for 7 h. The mixture was then cooled to 30° C. and the solvent was distilled off under vacuum to afford a red oil, to which dichloromethane (500 mL) was added. The mixture was stirred for 10 min, then filtered through silica gel (33.6 g). The filter cake was washed with dichloromethane (2 L). The combined filtrates were concentrated to dryness to yield T133-Y (mixture of E/Z-isomers) as red solid (124 g).

T133-Y (59 g, 0.45 mol) was stirred in acetone (800 mL) at 20° C. for 20 min, then iodomethane (97 g, 0.68 mol) was added dropwise at 20° C. The mixture was stirred for 72 h, then ethyl acetate (800 mL) was added. After 0.5 h, the precipitate (T133-X, mixture of E/Z-isomers) was isolated by filtration, washed with ethyl acetate and dried (dry product: 118 g).

T133-X (94 g, 0.35 mol) was stirred in methanol (1.0 L) at 20° C. for 20 min, then the mixture was cooled to 10° C. and sodium borohydride (26.1 g, 0.69 mol) was added portionwise within 2 h. After complete addition, the mixture was heated to 20° C. and stirred for 20 h. Then, the solvent was distilled of at 40° C. under vacuum. To the residue, water (300 mL) was added. The solution was extracted with ethyl acetate (4×200 mL). The combined organic layers were washed with brine (100 mL) and dried over sodium sulfate. In addition, activated charcoal (9 g) was added. The solids were removed by filtration, and the filtrate concentrated in vacuum to afford a first reduction product in the form of a first red oil (51 g).

The first red oil (50 g) was dissolved in THF (500 mL) in an autoclave. The mixture was hydrogenated with 10% Pd on charcoal (5 g) under 1.2 MPa $H_2$ pressure at 20° C. for 48 h. The mixture was then filtered through a Celite pad, and concentrated to afford a second reduction product in the form of a second red oil (50 g).

The second red oil (36 g) was dissolved in methanol saturated with $NH_3$ (700 mL) in an autoclave. A metal catalyst, in this case Raney-Nickel® (10 g, wet) was added. The mixture was hydrogenated under 1.2 MPa $H_2$ pressure at 20° C. for 48 h. The mixture was then filtered through a Celite pad, and concentrated to afford a yellow oil which was purified by vacuum distillation. The resulting crude product was again subjected to the hydrogenation (conditions as described above). After complete reaction (GC control), the mixture was filtered through a Celite pad, concentrated and purified by vacuum distillation to yield 3-(1-methylpiperidin-4-yl)propan-1-amine) (III-1) as colorless liquid (21 g).

Example 2. Synthesis of Ethyl 4-methyl-2-{[3-(1-methyl-4-piperidinyl)propyl]-amino}-5-pyrimidinecarboxylate (CAS 952494-43-8), Compound (IV-1)

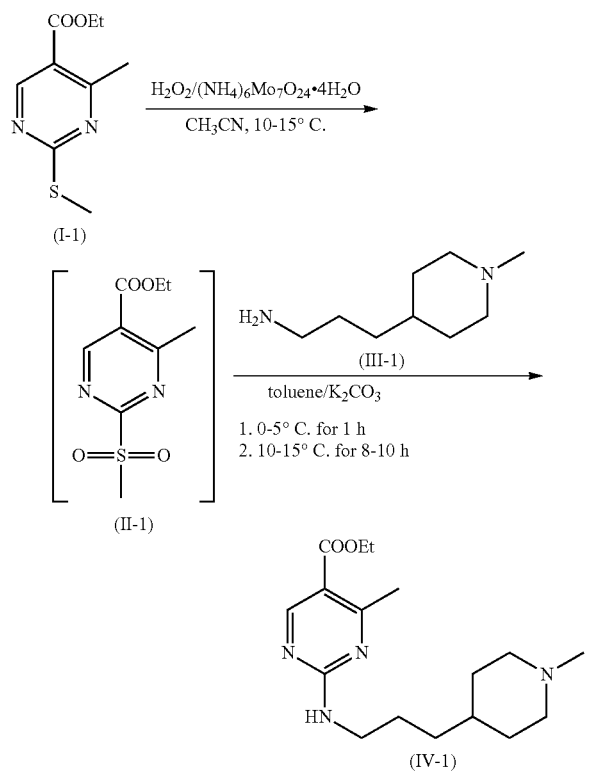

At 10° C., 4-methyl-2-methylsulfanyl-pyrimidine-5-carboxylic acid ethyl ester (106.0 g, 0.5 mol) and ammonium heptamolybdate $(NH_4)_6Mo_7O_{24}\cdot 4H_2O$ (6.18 g, 1 mol %) were added to acetonitrile (212.0 g) at 10° C. To the suspension, a solution of hydrogen peroxide 30% (122.5 g) in acetonitrile (424 g) was continuously dosed within 6-7 h while maintaining 10° C. After complete addition, the mixture was stirred at 10° C. for 12-16 h, then brine (212 g) and toluene (424 g) were added. After stirring for 0.5 h at 0-5° C., the organic layer was separated. To the aqueous layer, toluene (212 g) was added, and the mixture was stirred at 0-5° C. for 0.5 h, then the organic layer is separated. To the combined organic layers, brine (212 g) was added, and the mixture was stirred for 0.5 h at 0-5° C., then the aqueous layer was discarded. To the organic layer, 1% sodium sulfite in water (143 g) was added within 20 min. The biphasic mixture was stirred at 0-5° C. for 10 min, then the aqueous layer was discarded. To the organic layer, brine (212 g) was added, and the mixture was stirred for 0.5 h at 0-5° C., before the aqueous layer was discarded. The toluene layer containing the desired intermediate sulfone, 2-methanesulfonyl-4-methyl-pyrimidine-5-carboxylic acid ethyl ester, could be used in the next step without further purification.

Potassium carbonate (69.0 g, 0.5 mol) was added at 0-5° C. to the toluene solution. 3-(1-Methyl-piperidin-4-yl)-propylamine (69.0 g, 0.5 mol) was added over 20 min at 0-5° C., the suspension was then stirred for 1 h, before it was heated to 10-15° C. and stirred for 12-16 h. The solids were filtered off and the filter cake was washed with toluene (106 g). Water (212 g) was added to the filtrate, the biphasic mixture was stirred at 10-15° C. for 0.5 h, then the organic phase was separated. To the organic phase, 12% hydrochloric acid (750.0 g) were added over 30 min at 0-5° C., after stirring for 0.5 h, the aqueous phase, containing the product, was removed. Sodium hydroxide (20% in water) (533 g) were dosed to the product phase over 1 h at 0-5° C. to adjust the pH to 10-11, resulting in the precipitation of the product. The suspension was stirred for 2 h at 0-5° C., then the product, Ethyl 4-methyl-2-{[3-(1-methyl-4-piperidinyl)-propyl]amino}-5-pyrimidinecarboxylate, was isolated by centrifugation, washed with water and dried (147.6 g solid).

Example 3.1 Synthesis of 4-methyl-2-{[3-(1-methyl-4-piperidinyl)propyl]amino}-5-pyrimidinecarboxylic acid, Compound (IV-2)

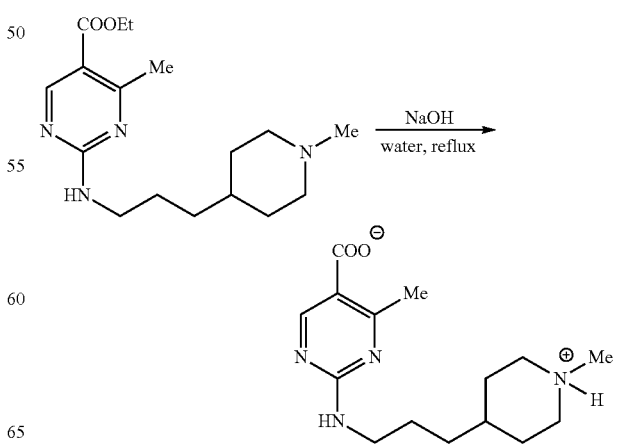

Ethyl 4-methyl-2-{[3-(1-methyl-4-piperidinyl)-propyl]-amino}-5-pyrimidine-carboxylate) (306 g, 0.94 mol) was mixed with water (750 g) and NaOH 50% in water (90 g, 1.13 mol). The mixture was heated to 95° C. and stirred for 1.5 h. The resulting solution was cooled to 40° C., HCl 37% aq. (37 g, 0.38 mol) were added, then seeding crystals of 4-methyl-2-{[3-(1-methyl-4-piperidinyl)propyl]amino}-5-pyrimidinecarboxylic acid (0.2 g) were added. The now turbid solution was stirred for 10 min, then additional HCl 37% aq. (74 g, 0.75 mol) were added over 1 h. The suspension was stirred at 40° C. for 1 h, then cooled to 10° C. within 5 h and stirred overnight. The product 4-methyl-2-{[3-(1-methyl-4-piperidinyl)propyl]amino}-5-pyrimidinecarboxylic acid was then isolated by filtration, washed with water and dried under vacuum at 50° C. (271 g, containing 6.2% water).

Example 3.2 Generation of Seed Material

Ethyl 4-methyl-2-{[3-(1-methyl-4-piperidinyl)-propyl]-amino}-5-pyrimidine-carboxylate) (50 g, 0.15 mol) was mixed with water (250 g) and KOH 50% in water (20.8 g, 0.19 mol). The mixture was heated to 95° C. and stirred for 1.5 h. It was then cooled to 40° C. and sodium chloride (75 g) was added. After stirring for 0.5 h, the solution was cooled to 20° C. and the pH adjusted to 7.5 with HCl 37% aq. (15.9 g). Compound (IV-2) started to precipitate after ca. 10 min. The pH was readjusted to 7.5 with 2N HCl, the resulting suspension was stirred at 20° C. overnight, then the pH was adjusted to 7 with 0.5 N HCl aq. (0.2 g), and the mixture was stirred another hour at 20° C., before the compound (IV-2) was isolated by centrifugation, washed with water and dried at 80° C. under vacuum (dry product: 46 g, ca. 87% w/w, where NaCl and residual water are primarily the impurity). The product was ground before being used further.

Example 3.3 Characterization of 4-methyl-2-{[3-(1-methyl-4-piperidinyl)propyl]amino}-5-pyrimidinecarboxylic Acid, Compound (IV-2)

NMR Data: $^1$H NMR (600 MHz, DMSO-d$_6$) δ ppm: 1.03-1.29 (m, 5H), 1.52 (quin, J=6.86 Hz, 2H), 1.61 (d, J=11.58 Hz, 2H), 1.89 (t, J=10.95 Hz, 2H), 2.17 (s, 3H), 2.52 (s, 3H), 2.77 (d, J=11.33 Hz, 2H), 3.28 (q, J=6.55 Hz, 2H), 7.69 (br. s., 1H), 8.63 (br. s., 1H). $^{13}$C NMR (101 MHz, DMSO-d$_6$) δ ppm: 24.29 (s, 1C), 26.02 (s, 1C), 31.56 (s, 2C), 33.15 (s, 1C), 34.12 (s, 1C), 40.69 (s, 1C), 45.73 (s, 1C), 55.14 (s, 2C), 112.55 (s, 1C), 160.81 (s, 1C), 162.08 (s, 1C), 166.81 (s, 1C), 169.17 (s, 1C).

HR-MS ([M+H]$^+$): Calculated: m/z=293.1972. Measured: m/z=293.1978.

Example 4

Synthesis of the mixture of Monoamides A (Compound V1-A2) and B (Compound V1-B2); (N-(2-amino-3,5-dimethylphenyl)-4-methyl-2-(3-(1-methylpiperidin-4-yl)propylamino)pyrimidine-5-carboxamide) and (N-(2-amino-4,6-dimethylphenyl)-4-methyl-2-(3-(1-methylpiperidin-4-yl)propylamino)pyrimidine-5-carboxamide), respectively.

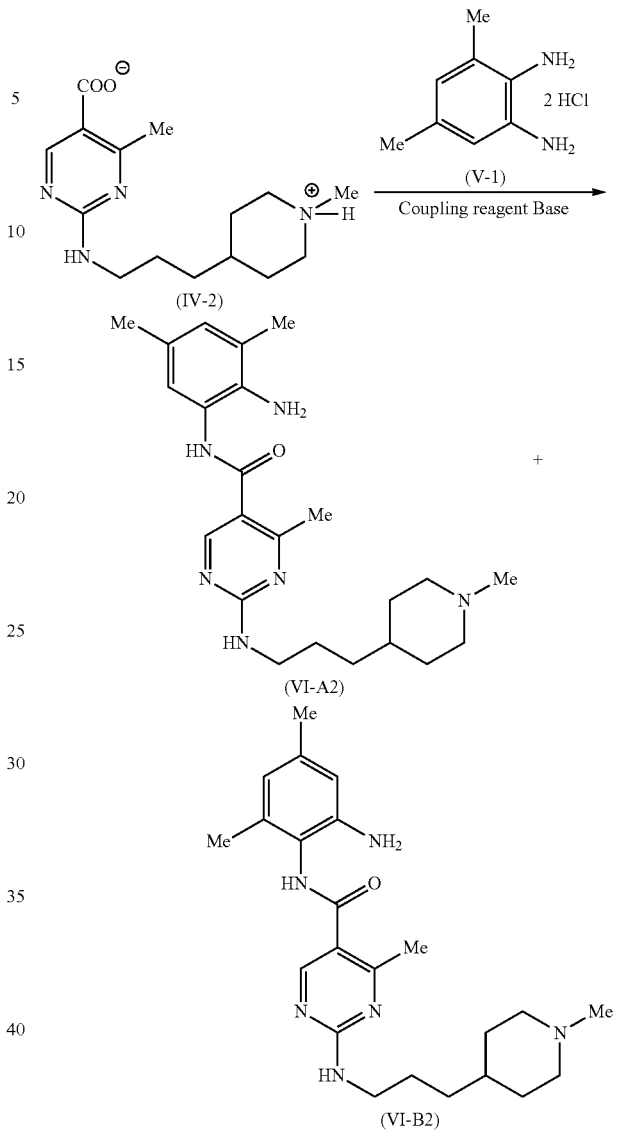

Example 4.1. Optimization

A variety of coupling reagents, conditions and solvents were screened. The best results under the specified conditions were achieved using PyBOP in DMF with Hünig's base. The table below provides an overview of some of the tested conditions. The screening experiments were done under argon in sealed tubes on mmol scale.

General procedure for the screening experiments: 4-methyl-2-{[3-(1-methyl-4-piperidinyl)propyl]amino}-5-pyrimidinecarboxylic acid (172 mg, 0.59 mmol) and 1,2-diamino-3,5-dimethylbenzene dihydrochloride (V-1) were charged to the reaction tube fitted with a magnetic stirring bar. DMF (2.5 mL) and Hünig's base were added, the tubes were sealed under inert atmosphere, then stirred at the temperatures shown in the table below, in which entries showing a range mean heating to the given upper temperature range. See the table below for an overview of some experiments that were done.

| Exp | Coupling reagent/Additive (Eq)(*) | V-1 (Eq) | Hünig's Base (Eq) | T [° C.] | t [h] | Reaction yield [%] |
|---|---|---|---|---|---|---|
| A-16 | PyBOP (1.3) | 1.3 | 3.2 | 20 | Over night | 91 |
| A-83 | PyBOP (1.3) | 1.3 | 2.9 | 20 → 60 | 2 | 92 |
| D-83 | TBTU (1.3) | 1.3 | 2.9 | 20 | Over night | 89 |
| A-84 | TBTU (1.3) | 1.3 | 2.9 | 20 → 60 | 3 | 91 |
| A-78 | DCC (1.4)/HOBt (1.1) | 1.3 | 3.2 | 20 | Over night | 64 |
| A-82-A | DCC (1.4)/HOBt (1.1) | 1.3 | 2.9 | 20 → 60 | 5 | 92 |
| A-2 | EDC HCl (1.4)/HOBt (1.1) | 1.3 | 3.2 | 20 | Over night | 88 |
| A-4 | EDC HCl (1.4)/HOBt (1.1) | 1.3 | 3.2 | 20 → 40 | Over night | 83 |

(*)Reading this column from top to bottom, entries A-16 through A-84 give amounts of coupling reagent in Eq, with no additive, and entries A-78 through A-4 give the coupling reagent-to-additive equivalent ratios. Each of the following four compounds is a compound referred to above as "coupling reagent":
PyBOP is (benzotriazol-1-yl-oxytripyrrolidinophosphonium hexafluorophosphate).
TBTU is O-(Benzotriazol-1-yl)-N,N,N',N'-tetramethyluronium tetrafluoroborate.
DCC is N,N'-Dicyclohexylcarbodiimide.
EDC HCl is 1-ethyl-3-(-3-dimethylaminopropyl) carbodiimide hydrochloride.
The compound HOBt is hydroxybenzotriazole, referred to above as "additive".

Another coupling reagent tested was CDI (1,1'-carbonyldiimidazole), in this case, the reaction proceeded to 5-(4,6-dimethyl-1H-benzimidazol-2-yl)-4-methyl-N-[3-(1-methyl-4-piperidinyl)propyl]-2-pyrimidinamine.

A solvent screen for the EDC-HCl conditions led to the identification as water/alcohol mixtures as solvent system with comparable yield and selectivity, which is advantageous as DMF is a non-preferred solvent. DMF is also more difficult to remove during work-up.

The table below provides a comparison of the coupling reagents at the respective best conditions identified during the initial screening phase.

| Coupling Reagent | Adavantages | Disadvantages | C | S | Y |
|---|---|---|---|---|---|
| PyBOP (520 g/mol) | No reaction with bisaniline Less sensitive to water | Quite expensive Waste Required solvents (DCM/DMF) | G | A | G |
| TBTU (320 g/mol) | Less sensitive to water More atom-efficient than PyBOP | Moderately expensive Required solvents (DCM/DMF) Lower yield (DCM) Side-reaction with bisaniline | G | A | B |
| EDC•HCl/HOBt (320 g/mol) | Coupling in water Water-soluble by-products | Moderately expensive Selectivity to be improved | G | A | G |
| DCC/HOBT (206 g/mol) | Inexpensive | Solvent (DMF) Insoluble DCU | G | A | NR |
| CDI (162 g/mol) | Inexpensive Atom-efficient Byproducts imidazole/CO$_2$ | Low reactivity of imidate with bisaniline Incomplete conversion Oil formation during rct/work-up | B | A | A |
| SOCl$_2$ (119 g/mol) | Inexpensive Atom-efficient (SO$_2$/HCl) | Acid chloride sensitive to water Incomplete conversion | B | A | A |

C: Conversion, S: Selectivity (Formation of bisamide impurity), Y: Isolated yield of free base; good (G), acceptable (A), below standard (B), rating not possible (NR); rating is based on a comparison of the overall results of the screening.

Further optimization of the EDC conditions showed that the reaction could be run without the additive HOBt, which is advantageous from an safety and environmental perspective (less waste, dry HOBT is hazardous) and also allows easier work-up.

Example 4.2. Optimized Procedure

4-Methyl-2-{[3-(1-methyl-4-piperidinyl)propyl]amino}-5-pyrimidinecarboxylic acid (450 g, 1.53 mol) and 1,2-diamino-3,5-dimethylbenzene dihydrochloride (388 g, 1.86 mol) were slurried in a mixture of water (3.73 L) and methanol (0.658 kg) at 20-25° C. under nitrogen inertization. After 30 min, the reaction mixture was cooled to −5° C. The pH was adjusted to 5.7 with 317 g of 45% aqueous potassium hydroxide. EDC-HCl (349 g, 1.82 mol) was added. The reaction mixture was stirred for 3 h at −5° C. with continuous pH adjustment to 5.7 with 2N HCl aq (total: 217 g). The reaction mixture was kept at −5° C. overnight, then water (3.30 kg) was added, and the mixture was heated to 50° C. The pH was adjusted to 10.5 with 372 g of 45% aqueous potassium hydroxide, causing precipitation of the product. The suspension was cooled to 20° C. and stirred for 90 min, before the mixture of the monoamides (VI-A2 and VI-B2) was isolated by centrifugation. The filter cake was washed with water, and the product dried in vacuum at 50° C. (dry product: 550 g).

The reaction described above also worked with ethanol instead of methanol.

The reaction described above also worked with a slightly different stoichiometry, 1.2 eq of the reagents works well—with less, selectivity will decrease.

Example 4.3

Characterization of Compound VI-A2: (N-(2-amino-3,5-dimethylphenyl)-4-methyl-2-(3-(1-methylpiperidin-4-yl)

propylamino)pyrimidine-5-carboxamide)¹H NMR (600 MHz, DMSO-$d_6$) δ ppm: 1.12 (qd, J=10.60, 2.64 Hz, 2H) 1.23 (q, J=7.00 Hz, 2H) 1.54 (quin, J=7.20 Hz, 2H) 1.61 (d, J=11.33 Hz, 2H) 1.81 (t, J=11.00 Hz, 2H) 2.10 (s, 3H) 2.13 (s, 3H) 2.15 (s, 3H) 2.44 (br. s., 3H) 2.72 (d, J=10.58 Hz, 2H) 3.29 (q, J=7.20 Hz, 2H) 4.12 (br. s., 3H) 6.37 (br. s., 1H) 6.67 (s, 1H) 6.90 (br. s., 1H) 7.04 (br. s., 2H) 8.44 (br. s., 2H) 9.25 (br. s., 2H). ¹³C NMR (151 MHz, DMSO-$d_6$) δ ppm: 17.83 (s, 1C) 20.03 (s, 1C) 22.76 (br. s., 1C) 26.15 (br. s., 1C) 32.00 (s, 2C) 33.33 (br. s., 1C) 34.47 (br. s., 1C) 40.71 (br. s., 1C) 46.25 (s, 1C) 55.50 (s, 2C) 117.84 (br. s., 1C) 122.73 (s, 1C) 123.01 (s, 1C) 124.09 (s, 1C) 124.41 (br. s., 1C) 128.10 (s, 1C) 138.00 (s, 1C) 157.40 (br. s., 1C) 161.68 (s, 1C) 165.26 (br. s., 1C) 166.53 (br. s., 1C).

HR-MS ([M+H]⁺): Calculated: m/z=411.2867; Measured: m/z=411.2841.

Example 4.4

Characterization of Compound VI-B2: (N-(2-amino-4,6-dimethylphenyl)-4-methyl-2-(3-(1-methylpiperidin-4-yl)propylamino)pyrimidine-5-carboxamide): ¹H NMR (600 MHz, DMSO-$d_6$) δ ppm 1.09 (qd, J=11.60, 3.40 Hz, 2H) 1.19-1.25 (m, 2H) 1.52 (quin, J=7.20 Hz, 2H) 1.59 (d, J=11.71 Hz, 2H) 1.78 (m, J=11.30, 11.30, 1.51 Hz, 2H) 2.05 (s, 3H) 2.10 (s, 3H) 2.13 (s, 3H) 2.42 (br. s., 3H) 2.70 (d, J=11.33 Hz, 2H) 3.27 (q, J=6.40 Hz, 4H) 4.39 (br. s., 1H) 4.68 (br. s., 1H) 6.28 (s, 1H) 6.40 (s, 1H) 7.44 (br. s., 1H) 8.37-8.65 (m, 1H) 9.08 (s, 1H).

HR-MS ([M+H]⁺): Calculated: m/z=411.2867; Measured: m/z=411.2887.

Example 5: Synthesis of 5-(4,6-dimethyl-1H-benzimidazol-2-yl)-4-methyl-N-[3-(1-methyl-4-piperidinyl)propyl]-2-pyrimidinamine, CAS 952494-46-1), Compounds VII-A2

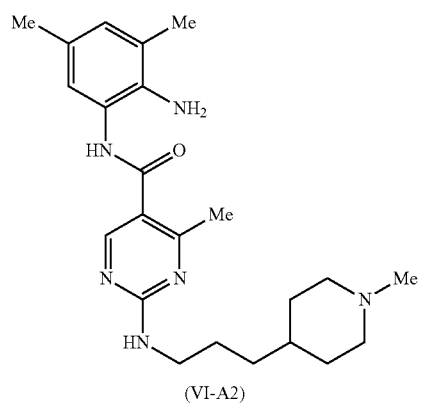

(VI-A2)

+

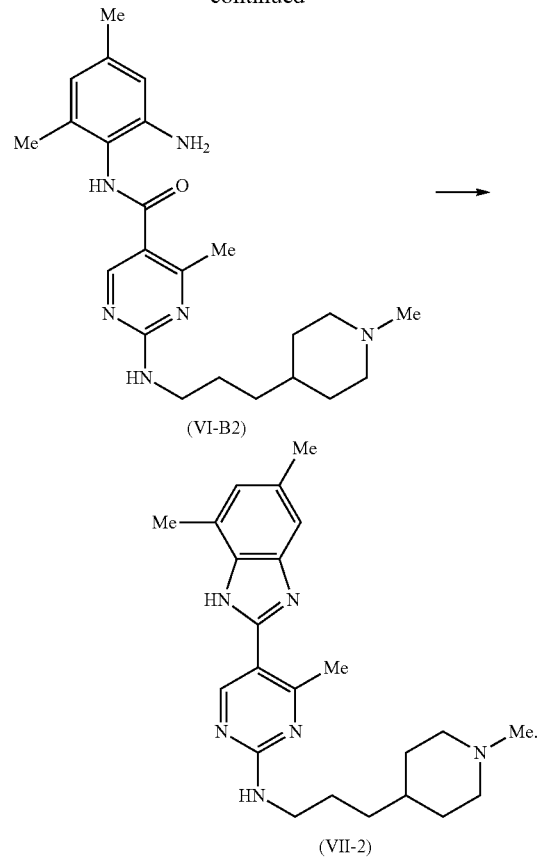

The reaction is done by heating the amide in acidic conditions. For this HCl or other acids, e. g., acetic acid could be used. Below, two representative conditions are described.

These reactions were run under inert conditions.

HCl Process:

Monoamides (VI-A2) and (VI-B2) (500 g, assay corrected: 1.12 mol) were slurried in water (3.21 L). The mixture was heated to 90° C., then HCl 37% aq. (440 g, 4.47 mol) were dosed within 30 min. After complete addition, the reaction mixture (pH<1) was kept at 90° C. for 3 h, then it was cooled to 20° C. The reaction mixture was kept at 20° C. overnight. 2-Methyl-THF (4.51 kg) was added to the aqueous solution, and the biphasic system was heated to 50° C. The pH was then adjusted to 10.5 with potassium hydroxide 45% in water (600 g, 4.81 mol). The mixture was stirred for 15 min, then the aqueous phase was removed and discarded. The organic layer was washed with water (595 g) for 15 min, before the aqueous phase was discarded. The organic layer was heated to 60° C. and cyclohexane (1.50 kg) was dosed over 45 min. The solution was then cooled to 53° C. and seeding crystals were added. The suspension was kept at 53° C. for 4 h, then cooled to 5° C. within 4 h and stirred overnight. The product (VII-2) was isolated by centrifugation, washed with a mixture of 2-methyl-THF and cyclohexane (3:1) and dried at 65-75° C. under vacuum (yield: 87%).

Acetic Acid Process:

Monoamides (VI-A2) and (VI-B2) (21.52 g, assay corrected: 47.6 mmol) were slurried in water (140.8 g). The mixture was heated to 90° C., then acetic acid (28.6 g, 476 mmol) were dosed within 15 min. The solution was stirred at 90° C. for 4 h, then it was cooled to 50° C. and 2-methyl-THF (160 g) was added. The pH was adjusted to 9.5 with potassium hydroxide 50% in water (60.11 g). After stirring for 10 min, the phases were separated and the aqueous layer discarded. The organic layer was washed with water (30 g) at 50° C. for 10 min, the aqueous layer was then discarded. The separation funnel was purged with 2-methyl-THF (35 g) which was combined in the reactor with the original organic layer. The 2-methyl-THF solution was heated to 60° C., then cyclohexane (65 g) was added over 15 min. The reaction mixture was cooled to 53° C. and seeding crystals were added. The resulting suspension was kept at 53° C. for 2 h, then it was cooled to 5° C. within 6 h and stirred overnight. The product, compound VII-2, was isolated by filtration, washed with a cold mixture of 2-methyl-THF and cyclohexane and dried at 50-60° C. under vacuum (yield: 86%).

In each case, the product identity was confirmed by comparison with known reference materials.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:
1. A method of synthesizing compound III-1

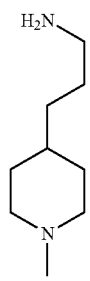

comprising coupling carboxylic acid-nitrile NC—CH$_2$—COOH with compound T133-RM13 yielding compound T133-U, and

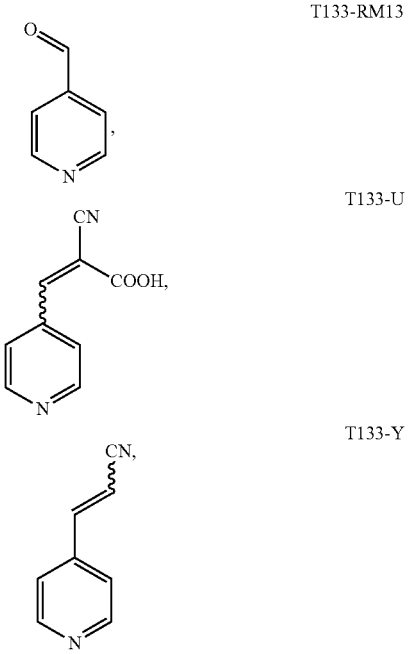

subsequently decarboxylating said compound T133-U to yield compound T133-Y.

2. A method of claim 1 further comprising reacting compound T133-Y with an alkyl iodide yielding compound T133-X

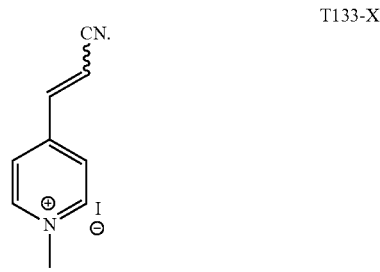

3. A method of claim 2, further comprising reducing compound T133-X to yield compound (III-1).

4. A method of claim 3, wherein said reducing comprises treating T133-X with sodium borohydride to yield a first reduction product; followed by hydrogenating said first reduction product with H$_2$ and palladium on carbon to yield a second reduction product; and subsequently treating said second reduction product with a metal catalyst and ammonia to yield compound III-1.

* * * * *